United States Patent
Jouy et al.

(10) Patent No.: US 11,471,384 B2
(45) Date of Patent: Oct. 18, 2022

(54) COMPOSITION COMPRISING AT LEAST TWO FATTY ACID ESTERS OF (POLY)GLYCEROL, AND USE THEREOF IN COSMETICS

(71) Applicant: L'OREAL, Paris (FR)

(72) Inventors: Chantal Jouy, Chevilly la Rue (FR); Emmanuelle Portois, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/343,510

(22) PCT Filed: Oct. 27, 2017

(86) PCT No.: PCT/EP2017/077599
§ 371 (c)(1),
(2) Date: Apr. 19, 2019

(87) PCT Pub. No.: WO2018/078095
PCT Pub. Date: May 3, 2018

(65) Prior Publication Data
US 2019/0240123 A1    Aug. 8, 2019

(30) Foreign Application Priority Data
Oct. 28, 2016   (FR) ...................... 16 60513

(51) Int. Cl.
| | |
|---|---|
| *A61K 8/39* | (2006.01) |
| *A61K 8/06* | (2006.01) |
| *A61Q 19/00* | (2006.01) |
| *A61K 8/81* | (2006.01) |
| *A61K 8/37* | (2006.01) |
| *A61K 8/58* | (2006.01) |
| *A61Q 19/08* | (2006.01) |
| *A61K 8/42* | (2006.01) |
| *A61K 8/891* | (2006.01) |

(52) U.S. Cl.
CPC .............. *A61K 8/068* (2013.01); *A61K 8/06* (2013.01); *A61K 8/37* (2013.01); *A61K 8/375* (2013.01); *A61K 8/39* (2013.01); *A61K 8/42* (2013.01); *A61K 8/585* (2013.01); *A61K 8/8152* (2013.01); *A61K 8/8158* (2013.01); *A61K 8/891* (2013.01); *A61Q 19/00* (2013.01); *A61Q 19/08* (2013.01); *A61K 2800/21* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 2005/0186169 A1* | 8/2005 | Charbit ................. | A61Q 19/08 424/70.16 |
| 2006/0159645 A1* | 7/2006 | Miller .................... | A61K 8/895 424/70.12 |

FOREIGN PATENT DOCUMENTS

| | | | | |
|---|---|---|---|---|
| DE | 20 2010 017 262 U1 | 8/2011 | | |
| JP | 2011-526900 A | 10/2011 | | |
| WO | WO 2010/002586 A2 | 1/2010 | | |
| WO | WO 2015/097029 | * 7/2014 | ............... | A61K 8/34 |
| WO | WO 2015/097029 | * 7/2015 | ............... | A61Q 3/00 |
| WO | WO 2015/097029 A1 | 7/2015 | | |
| WO | WO 2015/200488 | * 12/2015 | ............. | A01N 59/08 |
| WO | WO 2016/091939 A1 | 6/2016 | | |

OTHER PUBLICATIONS

Written Opinion of the International Searching Authority for PCT/EP2017/077599, dated Jan. 9, 2018.

* cited by examiner

*Primary Examiner* — Craig D Ricci
(74) *Attorney, Agent, or Firm* — Polsinelli PC

(57) ABSTRACT

The invention relates to a composition in the form of a nanoemulsion or microemulsion, comprising: —a first fatty acid ester of polyglycerol which is chosen from a fatty acid ester of polyglycerol formed from at least one acid comprising an alkyl or alkenyl chain containing from 12 to 20 carbon atoms and from 3 to 6 glycerol units; —a second fatty acid ester of (poly)glycerol (c) which is chosen from a fatty acid ester of (poly)glycerol formed from at least one acid comprising an alkyl or alkenyl chain containing from 6 to 18 carbon atoms and from 1 to 3 glycerol units; —at least one organopolysiloxane elastomer; —at least two acrylic acid-based polymers that are different from one another; —at least one amphiphilic polymer comprising at least one 2-acrylamidomethylpropanesulfonic acid (AMPS) unit; —at least one oil; —water. The invention also relates to a cosmetic treatment process for keratin materials such as the skin, by application of such a composition.

19 Claims, No Drawings

COMPOSITION COMPRISING AT LEAST TWO FATTY ACID ESTERS OF (POLY)GLYCEROL, AND USE THEREOF IN COSMETICS

CROSS REFERENCE TO RELATED APPLICATIONS

This application is a National Phase filing under 35 U.S.C. § 371 of PCT/EP2017/077599 filed on Oct. 27, 2017; and this application claims priority to Application No. 16 60513 filed in France on Oct. 28, 2016. The entire contents of each application are hereby incorporated by reference.

A subject of the present invention is a composition, in particular a cosmetic composition, in the form of a nanoemulsion or a microemulsion, comprising at least two different fatty acid esters of (poly)glycerol, at least one organopolysiloxane elastomer, at least two acrylic acid-based polymers that are different from one another, at least one amphiphilic polymer comprising at least one 2-acrylamidomethylpropane-sulfonic acid (AMPS) unit, at least one oil, and water, and the use of this composition for reducing the shininess and/or the sheen of facial and/or bodily skin.

The shininess of the skin may be linked to substantial secretion of sebum and/or sweat resulting from a physical activity or climatic conditions.

Indeed, the reflections caused by an excess of sebum and/or sweat on the surface of the skin are generally considered to be unattractive.

The currently proposed cosmetic compositions of a nanoemulsion or microemulsion comprising a high content of polyols and of fatty acid esters of (poly)glycerol have, when they are applied, sensory properties that can be tacky and/or may not give good slip.

Unexpectedly, it has been found, in the context of the present invention, that the particular compositions according to the invention described below make it possible to solve the abovementioned problems.

The inventors have in particular discovered, unexpectedly, that a composition in the form of a nanoemulsion or microemulsion comprising at least two different fatty acid esters of (poly)glycerol, at least two acrylic acid-based polymers that are different from one another, at least one amphiphilic polymer comprising at least one 2-acrylamidomethylpropanesulfonic acid (AMPS) unit, with at least one oil and with at least one organopolysiloxane elastomer, is stable and has in particular good sensory properties, such as less tackiness and/or more slip. These compositions make it possible in particular to reduce the shininess and/or the sheen of facial and/or bodily skin.

Consequently, the present invention relates to a composition in the form of a nanoemulsion or microemulsion, comprising:
- a first fatty acid ester of polyglycerol which is chosen from a fatty acid ester of polyglycerol formed from at least one acid comprising an alkyl or alkenyl chain containing from 12 to 20 carbon atoms and from 3 to 6 glycerol units;
- a second fatty acid ester of (poly)glycerol (c) which is chosen from a fatty acid ester of (poly)glycerol formed from at least one acid comprising an alkyl or alkenyl chain containing from 6 to 18 carbon atoms and from 1 to 3 glycerol units;
- at least one organopolysiloxane elastomer;
- at least two acrylic acid-based polymers that are different from one another;
- at least one amphiphilic polymer comprising at least one 2-acrylamidomethylpropanesulfonic acid (AMPS) unit;
- at least one oil;
- water.

The cosmetic composition according to the present invention can preferably be used for lotions and the like. Furthermore, the cosmetic composition according to the present invention may produce a pleasant texture and afford moisturizing properties and also increased suppleness. The composition, preferably the cosmetic composition, according to the present invention is described in greater detail hereinbelow.

A composition according to the invention comprising in particular at least two acrylic acid-based polymers that are different from one another, such as a crosslinked copolymer of $C_1$-$C_6$-alkyl acrylate and of (meth)acrylic acid and a crosslinked copolymer of $C_{10}$-$C_{30}$-alkyl acrylate and of (meth)acrylic acid, and at least one amphiphilic polymer comprising at least one 2-acrylamidomethylpropanesulfonic acid (AMPS) unit, such as the copolymer of AMPS and of ethoxylated stearyl methacrylate (25 EO), unexpectedly is stable while at the same time having tackiness and/or slip sensory properties that, after application to the skin, are better than those presented by similar compositions but which do not comprise the combination of the three polymers according to the invention.

The composition of the invention may be a cosmetic composition (i.e. intended for cosmetic purposes) or a dermatological composition. Preferentially, according to the invention, the composition is a cosmetic composition and even more preferentially a cosmetic composition for topical application.

The term "cosmetic composition" is in particular intended to mean a substance or a preparation intended to be brought into contact with the various superficial parts of the human body, in particular the epidermis, the bodily-hair and head-hair systems, the nails, the lips and the oral mucous membranes, with a view, exclusively or mainly, to cleansing them, making them more attractive, fragrancing them, modifying their appearance, protecting them, keeping them in good condition, or correcting body odours.

A subject of the present invention is also the cosmetic use of a composition as defined above, for reducing the shininess and/or the sheen of keratin materials such as facial and/or bodily skin.

Another subject of the present invention is a cosmetic treatment process for keratin materials such as the skin, characterized in that a composition as defined above is applied to the keratin materials, preferably the skin.

Fatty Acid Esters of (Poly)Glycerol

The composition according to the present invention comprises at least two fatty acid esters of (poly)glycerol that are different from one another.

The composition according to the invention comprises:
a) a first fatty acid ester of polyglycerol which is chosen from a fatty acid ester of polyglycerol formed from at least one acid comprising an alkyl or alkenyl chain containing from 12 to 20 carbon atoms and from 3 to 6 glycerol units, preferably from 5 to 6 glycerol units, and
b) a second fatty acid ester of (poly)glycerol which is chosen from a fatty acid ester of (poly)glycerol formed from at least one acid comprising an alkyl or alkenyl chain containing from 6 to 18 carbon atoms and from 1 to 3 glycerol units, preferably from 2 to 3 glycerol units.

The fatty acid esters of glycerol or polyglycerol used in the context of the present invention are non-ionic surfactants that are solid at a temperature of less than or equal to 45° C.

The compositions according to the invention comprise at least two fatty acid esters of glycerol or polyglycerol, which is optionally polyoxyalkylenated.

In the context of the present invention, mention may also be made of oxyalkylenated glycerol esters and in particular polyoxyethylenated derivatives of glyceryl esters of fatty acids and hydrogenated derivatives thereof. These oxyalkylenated glycerol esters can be chosen, for example, from glyceryl esters of fatty acids which are hydrogenated and oxyethylenated, such as PEG-200 hydrogenated glyceryl palmate, sold under the name Rewoderm LI-S 80 by the company Goldschmidt; oxyethylenated glyceryl cocoates, such as PEG-7 glyceryl cocoate, sold under the name Tegosoft GC by the company Goldschmidt, and PEG-30 glyceryl cocoate, sold under the name Rewoderm LI-63 by the company Goldschmidt; and mixtures thereof.

The (poly)glycerol esters according to the invention are glycerol esters (or monoglyceryl esters) or polyglycerol esters (or polyglyceryl esters) such as diglyceryl (or diglycerol) esters.

According to one embodiment, the (poly)glycerol ester according to the invention results from the esterification of at least one saturated or unsaturated fatty acid and of a (poly)glycerol.

The term "(poly)glycerol" denotes glycerol or glyceryl polymers. When it is a polymer, the polyglycerol is generally a linear sequence of 1 to 22 and preferably of 1 to 12 glycerol units.

In the context of the present invention, the term "polyoxyalkylenated (poly)glycerol" corresponds to polyoxyalkylenated ethers of glycerol (or of polyglycerol) and preferably polyoxyethylenated (or polyethylene glycol) ethers.

The esters more particularly considered according to the present invention are esters resulting from the esterification of poly(glycerol) and of $C_{12}$-$C_{20}$, preferably $C_{12}$ to $C_{18}$, preferably $C_{12}$, carboxylic acid(s), for the fatty acid esters of polyglycerol (a), such as lauric, oleic, stearic, isostearic and myristic acids.

The esters more particularly considered according to the present invention are esters resulting from the esterification of poly(glycerol) and of $C_6$-$C_{18}$, preferably $C_{12}$ to $C_{18}$, preferably $C_{10}$-$C_{12}$, carboxylic acid(s), for the fatty acid esters of polyglycerol (b), such as capric, caprylic or lauric acids.

The carboxylic acid may be linear or branched, and saturated or unsaturated. Preferably, it is a linear monocarboxylic acid.

In general, they are derived from the esterification of at least one hydroxyl function of a poly(glycerol) with a $C_{12}$-$C_{20}$, preferably $C_{12}$ to $C_{18}$, and more particularly $C_6$ to $C_{18}$, in particular $C_{10}$ to $C_{12}$, carboxylic acid.

According to a particular embodiment, the esters that are suitable for use in the present invention may be derived from the esterification of a poly(glycerol) with one or more identical or different carboxylic acids. It may be a hydroxylated monoester, a hydroxylated diester, a hydroxylated triester, or a mixture thereof.

A preferred cosmetic composition according to the invention comprises an ester of (poly)glycerol chosen from the group constituted of glycerol and glycerol polymers.

In one preferred embodiment of the invention, the first fatty acid ester of polyglycerol a) is chosen from polyglyceryl monolaurate comprising from 4 to 6 glycerol units, polyglyceryl monooleate comprising from 4 to 6 glycerol units, polyglyceryl mono(iso)stearate comprising from 4 to 6 glycerol units, polyglyceryl monolaurate comprising from 4 to 6 glycerol units, polyglyceryl dioleate comprising from 4 to 6 glycerol units, polyglyceryl monomyristate comprising from 4 to 6 glycerol units, and mixtures thereof.

In one preferred embodiment of the invention, the second fatty acid ester of (poly)glycerol b) is chosen from (poly)glyceryl monolaurate comprising from 1 to 3 glycerol units, (poly)glyceryl monocaprate comprising from 1 to 3 glycerol units, (poly)glyceryl monocaprylate comprising from 1 to 3 glycerol units, (poly)glyceryl monostearate comprising from 1 to 3 glycerol units, and mixtures thereof.

In another preferred embodiment of the invention, the first fatty acid ester of polyglycerol a) has an HLB (hydrophilic lipophilic balance) value of 10 to 13, and/or the second fatty acid ester of (poly)glycerol b) has an HLB value of 8 to 10.

Advantageously, the composition according to the invention comprises a first fatty acid ester of polyglycerol a) which is a polyglyceryl monolaurate comprising 4 to 6 glycerol units, in particular PG-5 laurate, and the second fatty acid ester of (poly)glycerol b) is chosen from (poly)glyceryl monolaurate comprising from 1 to 3 glycerol units and (poly)glyceryl monocaprate comprising from 1 to 3 glycerol units, and is preferably chosen from PG-2 laurate and PG-2 caprate.

Preferably, the fatty acid ester of (poly)glycerol (a) is chosen from a mixture of fatty acid esters of (poly)glycerol, in particular formed from 3 to 6 glycerol units, preferably formed from 5 or 6 glycerol units, and in which the mixture preferably comprises at least 30% or more of fatty acid esters of (poly)glycerol comprising 5 to 6 glycerol units.

Preferably, the starting material of fatty acid esters of (poly)glycerol (a) present in the composition of the invention comprises fatty acid esters of polyglycerols containing 70% or more of polyglycerols of which the degree of depolymerization is 4 or more, fatty acid esters of polyglycerols containing at most 30% of polymerization with a degree of polymerization of 5.

Esters chosen from monoglyceryl and/or diglyceryl caprylate, monoglyceryl and/or diglyceryl heptanoate, monoglyceryl and/or diglyceryl caprylate, propylene glycol caprylate and propylene glycol heptanoate, and mixtures thereof, are most particularly suitable for use in the invention.

It is more particularly monoglyceryl caprylate (also known as glyceryl caprylate) and mixtures thereof.

In a particularly advantageous manner, the composition according to the invention comprises:
as first fatty acid ester of polyglycerol, polyglyceryl-5 laurate, and/or
as second fatty acid ester of (poly)glycerol, polyglyceryl-2 laurate or polyglyceryl-2 caprate.

Polyglyceryl-5 laurate or PG-5 laurate is available under the trade name Laurate Sunsoft A-121E® by the company Taiyo Kagaku.

Polyglyceryl-2 laurate or PG-2 laurate is available under the trade name Sunsoft Q-12D-C® by the company Taiyo Kagaku.

Polyglyceryl-2 caprate or PG-2 caprate is available under the trade name Sunsoft Q-10D-C® by the company Taiyo Kagaku.

In the compositions according to the invention, the total amount of fatty acid ester(s) of (poly)glycerol (a) may be from 0.5% to 20% by weight, preferably from 1% to 10% by weight and more preferably from 2% to 9% by weight, relative to the total weight of the composition.

In the compositions according to the invention, the total amount of fatty acid ester(s) of (poly)glycerol (b) may be from 0.1% to 20% by weight, preferably from 1% to 10% by weight and more preferably from 1.5% to 7% by weight, relative to the total weight of the composition.

In the compositions according to the invention, the total amount of the fatty acid esters of (poly)glycerol (a) and (b) present ranges from 0.5% to 40% by weight, preferably from 2% to 20% by weight and more preferably from 3.5% to 16% by weight, relative to the total weight of the composition.

More particularly, in the compositions according to the invention, the [total amount of fatty acid ester(s) of polyglycerol (a)] to [total amount of fatty acid ester(s) of (poly)glycerol (b)] weight ratio ranges from 0.2 to 10, in particular from 0.3 to 5, preferably from 0.5 to 2.

Polyol

The composition according to the present invention comprises at least one polyol.

In one particular embodiment, the total amount of polyol(s) present in the composition according to the invention is greater than or equal to 15% by weight relative to the total weight of the composition.

According to the invention, the term "polyol" is intended to mean a hydrocarbon-based chain comprising at least two carbon atoms, preferably from 2 to 50 carbon atoms, preferably from 4 to 20 carbon atoms, preferably containing from 2 to 10 carbon atoms and preferentially containing from 2 to 6 carbon atoms, and bearing at least two hydroxyl groups. The polyols used in the present invention may have a weight-average molecular weight of less than or equal to 1000 and preferably between 90 and 500.

The polyol may be a natural or synthetic polyol. The polyol may have a linear, branched or cyclic molecular structure.

The polyol may be chosen from glycerol and derivatives thereof, and glycols and derivatives thereof. The polyol may be chosen from the group constituted of glycerol, diglycerol, polyglycerol, diethylene glycol, propylene glycol, dipropylene glycol, butylene glycol, pentylene glycol, hexylene glycol, 1,3-propanediol, 1,5-pentanediol, 1,2-octanediols, polyethylene glycols, in particular containing from 5 to 50 ethylene oxide groups, and sugars such as sorbitol, and a mixture thereof.

More particularly, the polyol may be chosen from the group constituted of dipropylene glycol and butylene glycol, and a mixture thereof.

Said polyol(s) may be present in a content ranging from 15% to 60% by weight, preferably ranging from 20% to 40% by weight and preferentially ranging from 20% to 30% by weight, relative to the total weight of the composition.

Oil

The cosmetic composition according to the present invention comprises at least one oil. According to the present invention, the term "oil" denotes a fatty compound or substance that is in the form of a liquid at ambient temperature (25° C.) and at atmospheric pressure (760 mmHg). As oils, those generally used in cosmetics may be used alone or in combinations thereof. These oils may be volatile or non-volatile, preferably non-volatile.

The oil may be a non-polar oil such as a hydrocarbon-based oil, a silicone oil or the like; a polar oil such as a plant or animal oil and an ester oil or an ether oil; or a mixture thereof.

It is preferable for the oil to be chosen from the group constituted of oils of plant origin, animal oils, synthetic oils, silicone oils and hydrocarbon-based oils.

Preferably, the cosmetic composition according to the present invention comprises at least one silicone oil, preferably at least two silicone oils that are different from one another.

As examples of plant oils, mention may be made, for example, of linseed oil, camellia oil, macadamia oil, corn oil, castor oil, olive oil, avocado oil, sasanqua oil, safflower oil, jojoba oil, sunflower oil, almond oil, rapeseed oil, sesame oil, soybean oil, groundnut oil, argan oil and apricot kernel oil, and mixtures thereof.

As examples of animal oils, mention may be made, for example, of squalene and squalane.

As examples of synthetic oils, mention may be made of alkanes such as isododecane and isohexadecane, fatty esters, fatty ethers and artificial $C_6$-$C_{22}$ acid triglycerides.

The fatty esters are preferably liquid esters of linear or branched, saturated or unsaturated $C_1$-$C_{26}$ aliphatic monoacids or polyacids and of linear or branched, saturated or unsaturated $C_1$-$C_{26}$ aliphatic monoalcohols or polyalcohols, the total number of carbon atoms in the fatty esters being greater than or equal to 10.

Preferably, for the monoalcohol esters, at least one from among the alcohol and the acid is branched.

Among the monoesters of monoacids and of monoalcohols, mention may be made of ethyl palmitate, ethylhexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-saccharide $C_4$-$C_{26}$ dihydroxy, trihydroxy, tetrahydroxy or pentahydroxy alcohols may also be used.

Mention may in particular be made of: diethyl sebacate; isopropyllauryl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; and diethylene glycol diisononanoate.

Fatty esters that may be used include sugar esters and diesters of $C_6$-$C_{30}$ and preferably $C_{12}$-$C_{22}$ fatty acids. It is recalled that the term "sugar" denotes hydrocarbon-based compounds comprising oxygen containing several alcohol functions, with or without aldehyde or ketone functions, and which comprise at least 4 carbon atoms. These sugars may be monosaccharides, oligosaccharides or polysaccharides.

Examples of suitable sugars that may be mentioned include saccharose (or sucrose), glucose, galactose, ribose, fucose, maltose, fructose, mannose, arabinose, xylose and lactose, and derivatives thereof, in particular alkyl derivatives such as methyl derivatives, for example methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may contain from one to three conjugated or unconjugated double bonds.

The esters according to this variant can also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, in particular, oleopalmitate, oleostearate and palmitostearate mixed esters, and also pentaerythrityl tetraethyl hexanoate.

More particularly, use is made of monoesters and diesters and in particular sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As preferred examples of fatty esters, mention may be made, for example, of diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethyl hexanoate, 2-ethylhexyl octanoate, 2-ethylhexyl caprylate/caprate, methyl palmitate, ethyl palmitate, isopropyl palmitate, ethylhexyl palmitate, isohexyl laurate, hexyl laurate, isocetyl stearate, isopropyl isostearate, isopropyl myristate, isodecyl oleate, glyceryl tris(2-ethyl hexanoate), pentaerythrityl tetrakis(2-ethylhexanoate), 2-ethylhexyl succinate and diethyl sebacate, and mixtures thereof.

As examples of artificial triglycerides, mention may be made, for example, of glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made, for example, of linear organopolysiloxanes such as dimethylpolysiloxane, methylphenylpolysiloxane, methylhydrogenopolysiloxane and the like; cyclic organopolysiloxanes such as octamethylcyclotetrasiloxane, decamethylcyclopentasiloxane, dodecamethylcyclohexasiloxane and the like; and mixtures thereof.

Preferably, the silicone oil is chosen from liquid polydialkylsiloxanes, in particular liquid polydimethylsiloxanes (PDMS) and liquid polyorganosiloxanes comprising at least one aryl group.

The polydialkylsiloxanes may be chosen from polydimethylsiloxanes comprising trimethylsilyl end groups, and polydimethylsiloxanes comprising dimethylsilanol end groups, known under the name dimethiconol (CTFA), and preferably polydimethylsiloxanes comprising trimethylsilyl end groups.

The polydialkylsiloxane chosen may be a mixture of dimethicone and dimethiconol (INCI name) available under the trade name Xiameter PMX-1503 FLUID® by the company Dow Corning.

These silicone oils may also be organomodified. The organomodified silicones that may be used according to the present invention are silicone oils as defined above comprising in their structure one or more organofunctional groups linked via a hydrocarbon-based group.

The organopolysiloxanes are defined in greater detail in Walter Noll's Chemistry and Technology of Silicones (1968), Academic Press. They may be volatile or non-volatile.

Volatile or non-volatile silicone oils, such as volatile or non-volatile polydimethylsiloxanes (PDMS) containing a linear or cyclic silicone chain, which are liquid or pasty at ambient temperature, in particular cyclopolydimethylsiloxanes (cyclomethicones) such as cyclohexasiloxane; polydimethylsiloxanes containing oxyethylene, alkyl, alkoxy or phenyl groups that are pendent or at the end of the silicone chain, said groups containing from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes, 2-phenyl ethyl trimethylsiloxysilicates and polymethylphenylsiloxanes, may be used.

The term "non-volatile silicone oil" is intended to mean a silicone oil that remains on the skin or the keratin fibre at ambient temperature and atmospheric pressure for at least several hours. These oils have in particular a vapour pressure of less than $10^{-3}$ mmHg (0.13 Pa).

Preferably, the organopolysiloxane is chosen from polydimethylsiloxanes containing oxyethylene groups. It is more particularly Bis-PEG-18 methyl ether dimethyl silane (INCI name).

Bis-PEG-18 methyl ether dimethyl silane is available under the trade name Dow Corning 2501 Cosmetic Wax® by the company Dow Corning.

As examples of volatile silicone oils that may be used in the invention, mention may be made of:

volatile linear or cyclic silicone oils, in particular those with a viscosity 8 centistokes ($8 \times 10^{-6}$ m$^2$/s) and in particular containing from 2 to 7 silicon atoms, these silicones optionally comprising alkyl or alkoxy groups having from 1 to 10 carbon atoms. As volatile silicone oil that can be used in the invention, mention may particularly made of octamethylcyclotetrasiloxane, decamethylcyclopentasiloxane or cyclopentasiloxane, dodecamethylcyclohexasiloxane or cyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane. Cyclohexasiloxane, or dodecamethylcyclohexasiloxane, is in particular available under the trade name Xiameter PMX-0246 Cyclohexasiloxane® by the company Dow Corning.

Cyclopentasiloxane, or decamethylcyclopentasiloxane, is in particular available under the trade name Xiameter PMX-0245 Cyclopentasiloxane® by the company Dow Corning.

The hydrocarbon-based oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, a liquid paraffin gel, polydecenes and hydrogenated polyisobutenes such as Parleam, and squalane.

As preferred examples of hydrocarbon-based oils, mention may be made, for example, of linear or branched hydrocarbons such as a mineral oil (for example liquid paraffin), paraffin, petroleum jelly or petrolatum, naphthalenes and the like; hydrogenated polyisobutene, isoeicosane, and a decene/butene copolymer; and mixtures thereof.

The oil may in particular be chosen from oils with a molecular weight of less than 600 g/mol.

The oil may be chosen from fatty esters containing one or more $C_1$-$C_{12}$ hydrocarbon-based chains (for example isopropyl myristate, isopropyl palmitate, isononyl isononanoate and ethylhexyl palmitate), hydrocarbon-based oils (for example isododecane, isohexadecane and squalane), oils of branched and/or unsaturated $C_{12}$-$C_{30}$ fatty alcohol type such as octyldodecanol or oleyl alcohol, and fatty ethers such as dicaprylyl ether.

Ethylhexyl palmitate is available under the trade name Palmitate d'ethyle 2 hexyle (DUB PO)® from the company Stéarinerie Dubois.

Particularly preferably, the composition according to the invention comprises one or more silicone oils; preferably, said composition comprises one or more silicone oils chosen from polydimethylsiloxanes containing oxyethylene groups, cyclopolydimethylsiloxanes (cyclomethicones) such as cyclohexasiloxane, and polydialkylsiloxanes such as polydimethylsiloxanes comprising trimethylsilyl end groups or polydimethylsiloxanes comprising dimethylsilanol end groups.

Preferably, the composition according to the invention comprises at least one polydimethylsiloxane containing oxyethylene groups, at least one cyclopolydimethylsiloxane, and at least one polydialkylsiloxane In the cosmetic composition according to the present invention the oil(s) may be present in a total content of from 0.50% to 80% by weight, in particular from 1% to 50% by weight, preferably from 1% to 20% by weight and more preferably from 2% to 15% by weight, relative to the total weight of the composition.

In one particular embodiment, the fatty acid ester(s) of (poly)glycerol and the oil(s), preferably the silicone oils, are present in a composition according to the invention, as defined above, in a [total amount of fatty acid ester(s) of (poly)glycerol/total amount of oil(s), preferably silicone oils] weight ratio which ranges from 0.2 to 10, in particular from 0.3 to 5, and preferably which ranges from 0.45 to 2.

Water

The cosmetic composition according to the present invention comprises water.

The amount of water is not limited, and may range from 30% to 90% by weight, preferably from 35% to 80% by weight and more preferably from 40% to 70% by weight relative to the total weight of the composition.

The composition according to the present invention may also comprise at least one additional surfactant other than the fatty acid ester(s) of (poly)glycerol (a) and (b) as defined above.

Non-Emulsifying Organopolysiloxane Elastomer

The cosmetic composition according to the present invention comprises at least one organopolysiloxane elastomer. According to the present invention, the organopolysiloxane elastomer which can be used as lipophilic gelling agent has the advantage of conferring good application properties on the composition according to the invention. It affords a very soft and mattifying feel after application, which is advantageous in particular for application to the skin. It may also allow efficient filling of the hollows present on keratin materials.

The term "organopolysiloxane elastomer" or "silicone elastomer" is intended to mean a supple, deformable organopolysiloxane with viscoelastic properties and in particular with the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer can be obtained by a crosslinking addition reaction of diorganopolysiloxane containing at least one hydrogen bonded to silicon and of diorganopolysiloxane having ethylenically unsaturated groups bonded to silicon, in particular in the presence of a platinum catalyst; or by a dehydrogenation crosslinking condensation reaction between a diorganopolysiloxane comprising hydroxyl end groups and a diorganopolysiloxane containing at least one hydrogen bonded to silicon, in particular in the presence of an organotin compound; or by a crosslinking condensation reaction of a diorganopolysiloxane comprising hydroxyl end groups and of a hydrolysable organopolysilane; or by thermal crosslinking of organopolysiloxane, in particular in the presence of an organic peroxide catalyst; or by crosslinking of organopolysiloxane via high-energy radiation, such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, in particular in the presence (C) of a platinum catalyst, as described, for instance, in application EP-A-295 886.

In particular, the organopolysiloxane elastomer may be obtained by reaction of dimethylpolysiloxane bearing dimethylvinylsiloxy end groups and of methylhydrogenopolysiloxane bearing trimethylsiloxy end groups, in the presence of a platinum catalyst.

Compound (A) is the base reactant for the formation of elastomeric organopolysiloxane, and the crosslinking takes place via an addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, in particular a linear-chain or branched-chain structure or a cyclic structure.

Compound (A) may have a viscosity at 25° C. ranging from 1 to 50 000 centistokes, in particular in order to be satisfactorily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from trimethylsiloxy-terminated methylhydrogenopolysiloxanes, trimethylsiloxy-terminated dimethylsiloxane/methylhydrogenosiloxane copolymers, and dimethylsiloxane/methylhydrogenosiloxane cyclic copolymers.

Compound (B) is advantageously a diorganopolysiloxane containing at least two lower (for example $C_2$-$C_4$) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxanemethylvinylsiloxane copolymers comprising dimethylvinylsiloxy end groups, dimethylsiloxane-methylvinylsiloxane copolymers comprising trimethylsiloxy end groups, dimethylsiloxane-methylphenylsiloxane-methylvinylsiloxane copolymers comprising trimethylsiloxy end groups, methyl(3,3,3-trifluoropropyl)polysiloxanes comprising dimethylvinylsiloxy end groups, and dimethylsiloxane-methyl(3,3,3-trifluoropropyl)siloxane copolymers comprising dimethylvinylsiloxy end groups.

In particular, the organopolysiloxane elastomer can be obtained by reaction of dimethylpolysiloxane comprising dimethylvinylsiloxy end groups and of methylhydrogenopolysiloxane comprising trimethylsiloxy end groups, in the presence of a platinum catalyst.

Advantageously, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is in particular chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1,000 parts by weight and better still from 1 to 100 parts by weight, as clean platinum metal, per 1,000 parts by weight of the total amount of compounds (A) and (B).

The elastomer is advantageously a non-emulsifying elastomer.

The term "non-emulsifying" defines organopolysiloxane elastomers not containing a hydrophilic chain and in particular not containing polyoxyalkylene units (in particular polyoxyethylene or polyoxypropylene units) or a polyglyceryl unit. Thus, according to a specific form of the invention, the composition comprises an organopolysiloxane elastomer devoid of polyoxyalkylene units and of polyglyceryl unit.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name) or Dimethicone Crosspolymer-3 (INCI name).

The organopolysiloxane elastomer particles may be conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are described in particular in patents EP 242 219, EP 285 886 and EP 765 656 and in application JP-A-61-194009.

The silicone elastomer is generally provided in the form of a gel, a paste or a powder but advantageously in the form of a gel in which the silicone elastomer is dispersed in a linear silicone oil (dimethicone) or cyclic silicone oil (e.g.: cyclopentasiloxane), advantageously in a linear silicone oil.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMSs) or dimethicones with a viscosity at 25° C. ranging from 1 to 500 cSt, optionally modified with optionally fluorinated aliphatic groups, or with functional groups such as hydroxyl, thiol and/or amine groups.

Mention may be made in particular of the compounds having the following INCI names:

Dimethicone/Vinyl Dimethicone Crosspolymer, such as USG-105 and USG-107A from the company Shin-Etsu; DC9506 and DC9701 from the company Dow Corning;

Dimethicone/Vinyl Dimethicone Crosspolymer (and) Dimethicone, such as KSG-6 and KSG-16 from the company Shin-Etsu;

Dimethicone/Vinyl Dimethicone Crosspolymer (and) Cyclopentasiloxane, such as KSG-15;

Cyclopentasiloxane (and) Dimethicone Crosspolymer, such as DC9040, DC9045 and DC5930 from the company Dow Corning;

Dimethicone (and) Dimethicone Crosspolymer, such as DC9041 from the company Dow Corning;

Dimethicone (and) Dimethicone Crosspolymer, such as Dow Corning EL-9240® Silicone Elastomer Blend from the company Dow Corning (mixture of polydimethylsiloxane crosslinked with hexadiene/polydimethylsiloxane (2 cSt));

$C_{4-24}$ Alkyl Dimethicone/Divinyl Dimethicone Crosspolymer, such as NuLastic Silk MA by the company Alzo;

Polysilicone-11 and Cyclohexasiloxane such as Gransil RPS-D6® from the company Grant Industries (comprising 87% of Cyclohexasiloxane and 13% of Polysilicone-11), Polysilicone-11 and isododecane such as Gransil PC-12® from the company Grant Industries (with a polysilicone-11:isododecane weight ratio of 13:87).

Mention may in particular be made, as examples of silicone elastomers dispersed in a linear silicone oil which can advantageously be used according to the invention, of the following references:

Dimethicone/Vinyl Dimethicone Crosspolymer (and) Dimethicone, such as KSG-6 and KSG-16 from the company Shin-Etsu;

Dimethicone (and) Dimethicone Crosspolymer, such as DC9041 from the company Dow Corning; and Dimethicone (and) Dimethicone Crosspolymer, such as Dow Corning EL-9240® silicone elastomer blend from Dow Corning (mixture of polydimethylsiloxane crosslinked with hexadiene/polydimethylsiloxane (2 cSt));

Diphenylsiloxy Phenyl Trimethicone (and) Dimethicone (and) Phenyl Vinyl Dimethicone Crosspolymer (INCI name), such as KSG 18A sold by the company ShinEtsu).

The particles of organopolysiloxane elastomers can also be used in powder form; mention may in particular be made of the powders sold under the names Dow Corning 9505 Powder and Dow Corning 9506 Powder by Dow Corning, these powders having the INCI name: Dimethicone/Vinyl Dimethicone Crosspolymer.

The organopolysiloxane powder may also be coated with silsesquioxane resin, as described, for example, in patent U.S. Pat. No. 5,538,793. Such elastomeric powders are sold under the names KSP-100, KSP-101, KSP-102, KSP-103, KSP-104 and KSP-105 by the company Shin-Etsu, and have the INCI name: Vinyl Dimethicone/Methicone Silsesquioxane Crosspolymer.

As examples of organopolysiloxane powders coated with silsesquioxane resin that may advantageously be used according to the invention, mention may in particular be made of the organopolysiloxane elastomers having the INCI name Vinyl Dimethicone/Methicone Silsesquioxane Crosspolymer, such as those sold under the commercial reference KSP-100 from the company Shin-Etsu.

As preferred lipophilic gelling agent of organopolysiloxane elastomer type, mention may be made in particular of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), Vinyl Dimethicone/Methicone Silsesquioxane Crosspolymer, Diphenylsiloxy Phenyl Trimethicone (and) Dimethicone (and) Phenyl Vinyl Dimethicone Crosspolymer (INCI name) and in particular the Dimethicone Crosspolymer (INCI name).

Particularly preferably, the silicone elastomer is chosen from a gel of silicone elastomer dispersed in a silicone oil as defined above, and preferably is polysilicone 11.

In particular, the silicone elastomer is Polysilicone-11 and Cyclohexasiloxane available under the trade name Gransil RPS-D6® from the company Grant Industries.

The total amount of silicone elastomer(s) in the cosmetic composition according to the present invention represents a content of active material of from 0.1% to 5% by weight, in particular from 0.2% to 3% by weight, preferably from 0.6% to 2% by weight and more preferably from 1.0% to 1.8% by weight, relative to the total weight of the composition.

Acrylic Acid-Based Polymers

The cosmetic composition according to the present invention comprises at least two acrylic acid-based polymers that are different from one another. According to the present invention, they may be chosen from acrylic acid derivatives. These polymers comprise:

from 80 mol % to 99 mol % of acrylic acid (AA) units of formula (5) below:

in which $X^+$ is a proton, an alkali metal cation, an alkaline-earth metal cation or the ammonium ion; and from 1 mol % to 20 mol % and preferably from 1 mol % to 15 mol % of units of formula (6) below:

in which $R_1$ denotes a hydrogen atom or a linear or branched $C_1$-$C_6$ alkyl radical (preferably methyl), A denotes an ester or amide group or an oxygen atom and $R_4$ denotes a linear or branched alkyl comprising m carbon atoms with m ranging from 6 to 30 and preferably from 10 to 25.

Preferably, the acrylic acid-based polymers present in the composition according to the invention are at least two crosslinked copolymers of $C_1$-$C_{30}$ alkyl acrylate and of (meth)acrylic acid, preferably a crosslinked copolymer of $C_1$-$C_6$ alkyl acrylate and of (meth)acrylic acid and a crosslinked copolymer of $C_{10}$-$C_{30}$ alkyl acrylate and of (meth)acrylic acid.

As acrylic acid-derived amphiphilic polymers that are preferred according to the present invention, mention may be made of:
 the non-crosslinked copolymer obtained from (meth)acrylic acid and steareth-20 methacrylate, sold under the name Aculyn 22° by the company Röhm & Haas,
 the non-crosslinked copolymer obtained from (meth)acrylic acid and laureth-25 methacrylate, sold under the name Aculyn 25® by the company Röhm & Haas,
 the non-crosslinked copolymer obtained from (meth)acrylic acid and beheneth-25 methacrylate, sold under the name Aculyn 28® by the company Röhm & Haas,
 the crosslinked copolymer obtained from (meth)acrylic acid and vinyl neodecanoate, sold under the name Aculyn 38® by the company Röhm & Haas,
 the crosslinked copolymer obtained from (meth)acrylic acid and steareth-20 methacrylate, sold under the name Aculyn 88® by the company Röhm & Haas,
 crosslinked copolymers of $C_{10}$-$C_{30}$ alkyl acrylate and of (meth)acrylic acid, for instance Pemulen TR1® and TR2® sold by the company Lubrizol,
 the crosslinked copolymer of acrylic acid and of vinyl isodecanoate, sold under the name Stabylen 30® by the company 3V,
 crosslinked copolymers obtained from (meth)acrylic acid and from a $C_{10}$-$C_{30}$ alkyl acrylate, sold under the name Carbopol ETD 2020® and Carbopol 1382® by the company Lubrizol,
 the non-crosslinked copolymer obtained from (meth)acrylic acid and steareth-20 itaconate, sold under the name Structure 2001® by the company National Starch,
 the non-crosslinked copolymer obtained from (meth)acrylic acid and ceteth-20 itaconate, sold under the name Structure 3001® by the company National Starch,
 the non-crosslinked copolymer obtained from (meth)acrylic acid, aminoacrylate and $C_{10}$-$C_{30}$ alkyl PEG 20 itaconate, sold under the name Structure Plus® by the company National Starch, and
 the non-crosslinked copolymer obtained from (meth)acrylic acid, methyl acrylate and ethoxylated alcohol dimethyl meta-isopropenyl benzyl isocyanate, sold under the name Viscophobe DB 1000® by the company Amerchol.

The acrylic acid-based polymer is in particular a non-crosslinked copolymer obtained from (meth)acrylic acid, methyl acrylate and ethoxylated alcohol dimethyl meta-isopropenyl benzyl isocyanate.

Preferably, said emulsifying polymer is chosen from acrylic acid-based polymers, and in particular crosslinked copolymers of $C_{10}$-$C_{30}$ alkyl acrylate and of (meth) acrylic acid, for instance Pemulen TR1® and TR2® sold by the company Noveon.

Mention may in particular be made of the crosslinked methacrylic acid/ethyl acrylate copolymer sold by the company Lubrizol under the trade name Carbopol Aqua SF-1, and/or the crosslinked copolymer of $C_{10}$-$C_{30}$ alkyl acrylate and of (meth)acrylic acid sold by the company Evonik under the name TEGO Carbomer 841 SER.

The total concentration of acrylic acid polymer preferably ranges from 0.2% to 5% by weight of active material relative to the total weight of the composition, preferably from 0.3% to 3% by weight of active material relative to the total weight of the composition and preferably from 0.4% to 1.5% by weight of active material relative to the total weight of the composition.

Amphiphilic Polymers Comprising at Least One 2-Acrylamidomethylpropanesulfonic Acid (AMPS) Unit The cosmetic composition according to the present invention comprises at least one amphiphilic polymer comprising at least one 2-acrylamidomethylpropanesulfonic acid (AMPS) unit.

According to the present invention, the amphiphilic polymers comprising at least one 2-acrylamidomethylpropanesulfonic acid (AMPS) unit, which are also known more simply as "amphiphilic AMPS polymers" hereinbelow, comprise both a hydrophilic part and a hydrophobic part comprising at least one fatty chain.

The fatty chain present in said amphiphilic AMPS polymers according to the invention may preferably comprise from 7 to 30 carbon atoms and more preferentially from 7 to 22 carbon atoms.

The amphiphilic AMPS polymers according to the invention are in particular chosen from amphiphilic polymers of at least one acrylamidomethylpropanesulfonic acid (AMPS) monomer and of at least one ethylenically unsaturated comonomer comprising at least one hydrophobic part containing from 7 to 30 carbon atoms and in particular from 7 to 22 carbon atoms or even from 12 to 22 carbon atoms.

The amphiphilic AMPS polymers according to the invention generally have a weight-average molecular weight ranging from 50 000 to 10 000 000 g/mol, in particular from 100 000 to 8 000 000 g/mol and even more particularly from 100 000 to 7 000 000 g/mol.

They may be crosslinked or non-crosslinked.

When the amphiphilic AMPS polymers according to the invention are crosslinked, the crosslinking agents may be chosen from the polyolefinically unsaturated compounds commonly used for the crosslinking of polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol di(meth)acrylate, tetraethylene glycol di(meth)acrylate, trimethylolpropane triacrylate, methylenebis(acrylamide), methylenebis(methacrylamide), triallylamine, triallyl cyanurate, diallyl maleate, tetraallylethylenediamine, tetraallyloxyethane, trimethylolpropane diallyl ether, allyl (meth) acrylate, allylic ethers of alcohols of the sugar series, or other allylic or vinyl ethers of polyfunctional alcohols, and also allylic esters of phosphoric and/or vinylphosphonic acid derivatives, or mixtures of these compounds.

The crosslinking agents may be chosen in particular from methylenebis(acrylamide), allyl methacrylate and trimethylolpropane triacrylate (TMPTA).

The degree of crosslinking may range, for example, from 0.01 mol % to 10 mol % and preferably from 0.2 mol % to 2 mol % relative to the polymer.

The amphiphilic AMPS polymers according to the invention may be chosen in particular from random amphiphilic AMPS polymers modified by reaction with a $C_6$-$C_{22}$ n-monoalkylamine or di-n-alkylamine, such as those described in patent application WO 00/31154.

An amphiphilic polymer that is suitable for use in the invention may comprise at least one ethylenically unsaturated hydrophilic monomer chosen, for example, from acrylic acid, methacrylic acid or substituted alkyl derivatives thereof or esters thereof obtained with monoalkylene or polyalkylene glycols, acrylamide, methacrylamide, vinylpyrrolidone, vinylformamide, maleic anhydride, itaconic acid or maleic acid, or mixtures thereof.

An amphiphilic polymer according to the invention may comprise at least one ethylenically unsaturated hydrophobic comonomer.

An amphiphilic polymer that is suitable for use in the invention may comprise at least one hydrophobic part chosen from saturated or unsaturated linear alkyl radicals, for instance n-octyl, n-decyl, n-hexadecyl, n-dodecyl and oleyl, branched alkyl radicals, for instance isostearic, or cyclic alkyl radicals, for instance cyclododecane or adamantine.

An amphiphilic AMPS polymer may also contain at least one ethylenically unsaturated hydrophobic comonomer comprising, for example:
- a fluoro or $C_7$-$C_{18}$ fluoroalkyl radical (for example the group of formula $(CH_2)_2$—$(CF_2)_9$—$CF_3$),
- a cholesteryl radical or a cholesterol-based radical (for example cholesteryl hexanoate),
- a polycyclic aromatic group, for instance naphthalene or pyrene,
- a silicone, alkylsilicone or alkylfluorosilicone radical.

These copolymers are in particular described in document EP-A-750 899, patent U.S. Pat. No. 5,089,578 and in the following publications by Yotaro Morishima:
- Self-assembling amphiphilic polyelectrolytes and their nanostructures, Chinese Journal of Polymer Science, Vol. 18, No. 40, (2000), 323-336;
- Micelle formation of random copolymers of sodium 2-(acrylamido)-2-methylpropanesulfonate and a nonionic surfactant macromonomer in water as studied by fluorescence and dynamic light scattering, Macromolecules, 2000, Vol. 33, No. 10 3694-3704;
- Solution properties of micelle networks formed by nonionic moieties covalently bound to a polyelectrolyte: salt effects on rheological behavior—*Langmuir,* 2000, Vol. 16, No. 12, 5324-5332;
- Stimuli responsive amphiphilic copolymers of sodium 2-(acrylamido)-2-methylpropanesulfonate and associative macromonomers, Polym. Preprint, Div. Polym. Chem. 1999, 40(2), 220-221.

They are also described in documents EP 1 069 142, WO 02/44224, WO 02/44225, WO 02/44227, WO 02/44229, WO 02/44230, WO 02/44231, WO 02/44267, WO 02/44268, WO 02/44269, WO 02/44270, WO 02/44271, WO 02/43677, WO 02/43686, WO 02/43687, WO 02/43688 and WO 02/43689, in the name of Clariant.

An ethylenically unsaturated hydrophobic comonomer of the invention may preferably be chosen from the acrylates or acrylamides of formula (1) below:

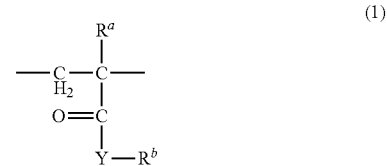

in which:
Ra denotes a hydrogen atom or a linear or branched $C_1$-$C_6$ alkyl radical, preferably methyl;
Y denotes O or NH;
Rb denotes a hydrophobic radical comprising a fatty chain containing from 7 to 30 carbon atoms, preferably from 7 to 22 and more particularly from 12 to 22 carbon atoms.

The hydrophobic radical Rb is chosen from saturated or unsaturated linear $C_7$-$C_{22}$ alkyl radicals (for example n-octyl, n-decyl, n-hexadecyl, n-dodecyl or oleyl), branched alkyl radicals (for example isostearic) or cyclic alkyl radicals (for example cyclododecane or adamantane); $C_7$-$C_{18}$ alkyl-perfluoro radicals (for example the group of formula —$(CH_2)_2(CF_2)_9$—$CF_3$); the cholesteryl radical or a cholesterol ester, for instance cholesteryl hexanoate; aromatic polycyclic groups, for instance naphthalene or pyrene.

Among these radicals, linear and branched alkyl radicals are more particularly preferred.

According to one preferred embodiment of the invention, the hydrophobic radical Rb may also comprise at least one alkylene oxide unit and preferably a polyoxyalkylene chain.

The polyoxyalkylene chain may preferentially be constituted of ethylene oxide units and/or propylene oxide units and even more particularly be constituted solely of ethylene oxide units.

The number of moles of oxyalkylene units may generally range from 1 to 30 mol, more preferentially from 1 to 25 mol and even more preferentially from 3 to 20 mol.

Among these polymers, mention may be made of:
crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl (meth)acrylate units relative to the polymer, such as those described in application EP-A-750 899;

terpolymers comprising from 10 mol % to 90 mol % of acrylamide units, from 0.1 mol % to 10 mol % of AMPS units and from 5 mol % to 80 mol % of n($C_6$-$C_{18}$)alkylacrylamide units relative to the polymer, such as those described in U.S. Pat. No. 5,089,578;

non-crosslinked copolymers of partially or completely neutralized AMPS and of n-dodecyl methacrylate, n-hexadecyl methacrylate or n-octadecyl methacrylate, such as those described in the Morishima articles mentioned above;

crosslinked or non-crosslinked copolymers of partially or completely neutralized AMPS and of n-dodecylmethacrylamide, such as those described in the Morishima articles mentioned above.

Amphiphilic AMPS polymers that may also be mentioned include copolymers of totally neutralized AMPS and of n-dodecyl, n-hexadecyl and/or n-octadecyl methacrylate, and also non-crosslinked and crosslinked copolymers of AMPS and of n-dodecylmethacrylamide.

Mention will be made more particularly of crosslinked or non-crosslinked amphiphilic AMPS copolymers constituted of:
(a) 2-acrylamido-2-methylpropanesulfonic acid (AMPS) units of formula (2) below:

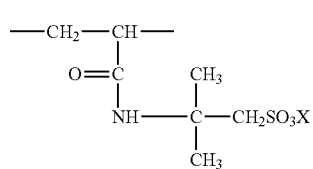

(2)

in which X is a proton, an alkali metal cation, an alkaline-earth metal cation or the ammonium ion;

(b) and units of formula (3) below:

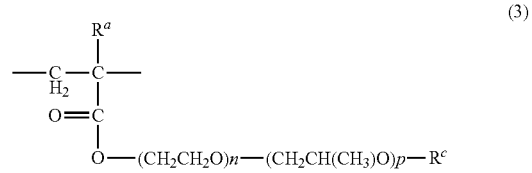

(3)

in which n and p, independently of one another, denote a number of moles and range from 0 to 30, preferably from 1 to 25 and more preferably from 3 to 20, with the proviso that n+p is less than or equal to 30, preferably less than 25 and better still less than 20; Ra denotes a hydrogen atom or a linear or branched $C_1$-$C_6$ alkyl radical, preferably methyl, and Rc denotes a linear or branched alkyl containing from 7 to 22 carbon atoms and preferably from 12 to 22 carbon atoms.

In formula (2), the cation X more particularly denotes sodium or ammonium. Among the monomers of formula (3), mention may be made of—esters of (meth)acrylic acid and of a $C_{10}$-$C_{18}$ fatty alcohol polyoxyethylenated with 8 EO, for instance the product Genapol C-080® sold by the company Clariant, esters of (meth)acrylic acid and of a $C_{11}$ fatty oxo alcohol polyoxyethylenated with 8 EO, for instance the product Genapol UD-080® sold by the company Clariant, esters of (meth)acrylic acid and of a $C_{12}$-$C_{14}$ polyoxyethylenated fatty alcohol with 7 EO, for instance the product Genapol LA-070® sold by the company Clariant, esters of (meth)acrylic acid and of a $C_{12}$-$C_{14}$ polyoxyethylenated fatty alcohol with 11 EO, for instance the product Genapol LA-110® sold by the company Clariant, esters of (meth)acrylic acid and of a $C_{16}$-$C_{18}$ polyoxyethylenated fatty alcohol with 8 EO, for instance the product Genapol T-080® sold by the company Clariant, esters of (meth)acrylic acid and of a $C_{16}$-$C_{18}$ polyoxyethylenated fatty alcohol with 15 EO, for instance the product Genapol T-150® sold by the company Clariant, esters of (meth)acrylic acid and of a $C_{16}$-$C_{18}$ polyoxyethylenated fatty alcohol with 11 EO, for instance the product Genapol T-110® sold by the company Clariant, esters of (meth)acrylic acid and of a $C_{16}$-$C_{18}$ polyoxyethylenated fatty alcohol with 20 EO, for instance the product Genapol T-200® sold by the company Clariant, esters of (meth)acrylic acid and of a $C_{16}$-$C_{18}$ polyoxyethylenated fatty alcohol with 25 EO, for instance the product Genapol T-250® sold by the company Clariant, esters of (meth)acrylic acid and of a $C_{18}$-$C_{22}$ polyoxyethylenated fatty alcohol with 25 EO and/or of a $C_{16}$-$C_{18}$ polyoxyethylenated fatty isoalcohol with 25 EO.

The products that will be chosen more particularly are:
i. non-crosslinked products for which p=0, n=7 or 25, Ra denotes methyl and Rc represents a $C_{12}$-014 or $C_{16}$-$C_{18}$ alkyl mixture,
ii. crosslinked products for which p=0, n=8 or 25, Ra denotes methyl and Rc represents a $C_{16}$-$C_{18}$ alkyl mixture.

These polymers are described and synthesized in application EP 1 069 142.

These particular amphiphilic AMPS polymers may be obtained according to the standard processes of free-radical polymerization in the presence of one or more initiators, for instance azobisisobutyronitrile (AIBN), azobisdimethylvalero-nitrile, 2,2-azobis(2-amidinopropane) hydrochloride (ABAH), organic peroxides such as dilauryl peroxide, benzoyl peroxide or tert-butyl hydroperoxide, mineral peroxide compounds such as potassium or ammonium persulfate, or $H_2O_2$ optionally in the presence of reducing agents.

These amphiphilic AMPS polymers may be obtained in particular by free-radical polymerization in tert-butanol medium, in which they precipitate. By using precipitation polymerization in tert-butanol, it is possible to obtain a size distribution of the polymer particles that is particularly favourable for its uses.

The reaction may be performed at a temperature of between 0 and 150° C. and preferably between 10 and 100° C., either at atmospheric pressure or under reduced pressure.

It may also be performed under inert atmosphere and preferably under nitrogen. The amphiphilic AMPS polymers according to the invention may preferably be partially or totally neutralized with a mineral base such as sodium hydroxide, potassium hydroxide, aqueous ammonia or an organic base such as monoethanolamine, diethanolamine, triethanolamine, an aminomethylpropanediol, N-methylglucamine, basic amino acids, for instance arginine and lysine, and mixtures of these compounds. They may in particular be totally or almost totally neutralized, i.e. at least 80% neutralized.

The molar percentage concentration of the units of formula (2) and of the units of formula (3) in the amphiphilic AMPS polymers according to the invention may vary as a function of the desired cosmetic application, for example the nature of the emulsion (oil-in-water or water-in-oil emulsion) and the desired rheological properties of the formulation. It may range, for example, between 0.1 mol % and 99.9 mol %. The sparingly hydrophobic amphiphilic AMPS polymers according to the invention will be more suitable for thickening and/or stabilizing oil-in-water emulsions. The molar proportion of units of formula (3) may then preferably range from 0.1 mol % to 50 mol %, more particularly from 1 mol % to 25 mol % and even more particularly from 3 mol % to 10 mol %.

The more hydrophobic amphiphilic AMPS polymers according to the invention will be more suitable for thickening and/or stabilizing water-in-oil emulsions. The molar proportion of units of formula (3) may then preferably range from 50.1 mol % to 99.9 mol %, more particularly from 60 mol % to 95 mol % and even more particularly from 65 mol % to 90 mol %.

The distribution of the monomers in the amphiphilic AMPS polymers according to the invention may be, for example, alternate, block (including multiblock) or random. As a guide, and without this being limiting, mention may be made in particular of the copolymer of AMPS and of ethoxylated $C_{12}$-$C_{14}$ alcohol methacrylate (non-crosslinked copolymer obtained from Genapol LA-070 and from AMPS) (CTFA name: Ammonium Acryloyldimethyltaurate/Laureth-7 methacrylate copolymer) sold under the name Aristoflex LNC® by the company Clariant, the copolymer of AMPS and of ethoxylated (25 EO) stearyl methacrylate (copolymer crosslinked with trimethylolpropane triacrylate, obtained from Genapol T-250 and from AMPS) (CTFA name: Ammonium Acryloyldimethyltaurate/Steareth-25 Methacrylate Crosspolymer) sold under the name Aristoflex HMS® by the company Clariant, Aristoflex SNC (80/20 copolymer of AMPS/ethoxylated (8 mol EO) C16-C18 alcohol methacrylate; CTFA name: Ammonium Acryloyldimethyltaurate/Steareth-8 methacrylate copolymer) and Aristoflex HMB® (copolymer of AMPS/ethoxylated (25 EO) behenyl methacrylate, crosslinked with trimethylolpropane triacrylate (TMPTA)).

Preferably, the composition comprises an amphiphilic polymer comprising at least one 2-acrylamidomethylpropanesulfonic acid (AMPS) unit which is the copolymer of AMPS and of ethoxylated (25 EO) stearyl methacrylate (copolymer crosslinked with trimethylolpropane triacrylate, obtained from Genapol T-250 and from AMPS) (CTFA name: Ammonium Acryloyldimethyltaurate/Steareth-25 Methacrylate Crosspolymer) sold under the name Aristoflex HMS® by the company Clariant.

The emulsifying polymer(s) that are suitable for use in the invention are generally present in the composition in an amount of from 0.1% to 3% by weight relative to the total weight of the composition, preferably from 0.1% to 1% by weight relative to the total weight of the composition and better still 0.3% to 0.8% by weight relative to the total weight of the composition.

In one particular embodiment, the organopolysiloxane elastomer(s) and the acrylic acid-based polymers and the amphiphilic polymer(s) are present in a composition according to the invention as defined above, in a weight ratio of active matter of [total amount of organopolysiloxane elastomer(s)/total amount of acrylic acid-based polymers and of amphiphilic polymer(s)] which ranges from 0.01 to 20, in particular from 0.3 to 10, and preferably from 0.5 to 3.

Additional Anionic Surfactant

The composition according to the present invention may also comprise at least one additional anionic surfactant other than the fatty acid ester(s) of (poly)glycerol (a) and (b) as defined above.

The composition of the present invention may comprise at least one sulfonate salt (fatty acid amide) anionic surfactant.

Said anionic surfactants(s) is (are) at least one sulfonate salt (fatty acid amide) surfactant represented by formula (II) below:

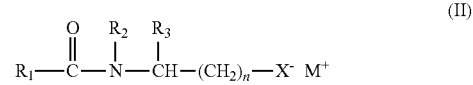

in which:
$R_1$ is a saturated or unsaturated, linear or branched alkyl chain having from 7 to 17 carbon atoms,
$R_2$ is H or a methyl group,
$R_3$ is H, COO$^-$M+, M CH$_2$COO$^-$ or COOH,
n is 0 to 2,
X represents COO or SO$_3^-$ and
M represents independently H, sodium, potassium or sorbitan, and mixtures thereof.

Such anionic surfactant agents are those described in EP 2 335 681.

Preferably, the anionic surfactants (f) are chosen from surfactants of the type taurate, glutamate, alanine or alaninate, sarcosinate, aspartate, and mixtures thereof.

Preferably, the anionic surfactants are surfactants of the type taurate, glutamate, sarcosinate and/or mixtures thereof.

Particularly preferably, the anionic surfactants (f) are taurate surfactants.

In particular, the taurate surfactants are according to general formula (III)

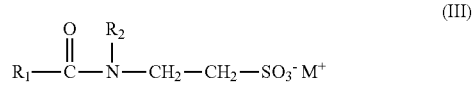

in which:

$R_1$ is preferably a saturated or unsaturated, linear or branched alkyl chain with from 7 to 17 carbon atoms, and more preferably from 9 to 13 carbon atoms, $R_2$ is H or a methyl group, and M is H, sodium or potassium.

The anionic surfactants of formula (III) can be chosen from potassium cocoyltaurate, potassium methylcocoyltaurate, sodium caproylmethyltaurate, sodium cocoyltaurate, sodium lauroyltaurate, sodium methylcocoyltaurate, sodium methyllauroyltaurate, sodium methylmyristoyltaurate, sodium methyloleoyltaurate, sodium methylpalmitoyltaurate, and sodium methylstearoyltaurate, and mixtures thereof. More particularly, the ionic surfactant(s) of formula (II) are chosen from potassium cocoyltaurate, potassium methylcocoyltaurate, sodium cocoyltaurate, sodium lauroyltaurate, sodium methylcocoyltaurate and sodium methyllauroyltaurate, and mixtures thereof.

The compositions of the present invention may also comprise mixtures of anionic surfactants of amino acid type, such as the mixture of anionic surfactants of glutamate and taurate type, a mixture of taurates, or a mixture of surfactants of glutamate and sarcosinate type.

The term "anionic surfactant of amino acid type" is intended to mean surfactants which are derived from taurate, glucamate, alanine or alaninate, sarcosinate and aspartate.

With the amino acid surfactant agent, in particular the surfactant agents, this is intended to mean taurate, glucamate, alanine or alaninate, sarcosinate and aspartate derivatives.

According to one embodiment of the invention, at least one anionic surfactant is chosen from the group constituted of an isethionate, a taurate, a sarcosinate, a sulfosuccinate, a sulfoacetate, a glycinate, a glutamate and a carboxylate, in which at least one anionic surfactant has a $C_8$ to $C_{20}$ alkyl chain, and a solubilizing counter-cation chosen from sodium, potassium and ammonium.

According to one embodiment of the invention, at least one anionic surfactant agent is a taurate, said taurate having a $C_8$ to $C_{20}$ alkyl chain, and a solubilizing counter-cation chosen from sodium, potassium and ammonium.

According to one embodiment of the invention, at least one anionic surfactant agent is chosen from the group constituted of sodium laurylmethylisethionate, sodium methyloleoyltaurate, sodium N-myristoyl-N-methyltaurate, sodium (coconut fatty acid)methyltaurate and sodium laurylmethyltaurate.

According to one particularly preferred embodiment of the invention, the anionic surfactant is an anionic surfactant of formula (II) in which $R_2$ is a methyl, $R_1$ is a saturated linear alkyl chain having 17 carbon atoms, and M is sodium, i.e. sodium N-methylstearoyltaurate. Sodium N-methylstearoyltaurate is available under the trade name Nikkol SMT® by the company Nikko.

The total amount of the anionic surfactant(s) of formula (II), preferably of formula (III), may be from 0.01% to 2% by weight, in particular from 0.05% to 1% by weight, preferably from 0.08% to 0.5% by weight, relative to the total weight of the composition according to the invention.

Thickener

The cosmetic composition according to the present invention may also comprise at least one thickener.

The thickener may be chosen from organic and inorganic thickeners.

The thickener is preferably chosen from associative thickeners and polysaccharides such as starch and xanthan gum.

In the present context, the term "associative thickener" denotes an amphiphilic thickener comprising both hydrophilic and hydrophobic units, for example comprising at least one $C_8$-$C_{30}$ fatty chain and at least one hydrophilic unit.

The viscosity of the cosmetic composition according to the present invention is not particularly limited. The viscosity may be measured at 25° C. with viscometers or rheometers, preferably having cone-plate geometry. Preferably, the viscosity of the cosmetic composition according to the present invention may be, for example, from 1 to 2000 Pa·s and preferably from 1 to 1000 Pa·s at 25° C. and 1 s$^{-1}$.

The thickener may be present in an amount in the range from 0.001% to 10% by weight and preferably from 0.01% to 10% by weight, for example from 0.1% to 5% by weight, relative to the total weight of the composition.

Other Components

The cosmetic composition according to the present invention may also comprise an efficient amount of other components, previously known elsewhere in compositions, in particular cosmetic compositions, such as various adjuvants, anti-ageing agents, depigmenting agents, moisturizing agents, anti-greasy skin agents, sequestrants such as EDTA and etidronic acid, UV stabilizers, preservatives (such as phenoxyethanol), vitamins or provitamins, for example, opacifiers, fragrances, plant extracts, cationic polymers, etc.

Preparation and Properties

The cosmetic composition according to the present invention may be prepared by mixing the essential and optional components above according to a conventional process. The conventional process comprises mixing with a high-pressure homogenizer (a high-energy process). As a variant, the cosmetic composition may be prepared via a low-energy process such as a phase inversion temperature (PIT) process, a phase inversion concentration (PIC), self-emulsification, and the like. Preferably, the cosmetic composition is prepared via a low-energy process.

In a particular embodiment, the weight ratio between the total amount of the fatty acid esters of (poly)glycerol defined in (a) and (b) and the oil (d) in a composition according to the invention as defined above ranges from 0.50 to 10, preferably from 1 to 5.

The cosmetic composition according to the present invention is in the form of a nanoemulsion or microemulsion.

The term "microemulsion" may be defined in two ways, i.e. in a broad sense and in a narrower sense. Namely, in one case ("microemulsion in the narrow sense"), the term microemulsion denotes a thermodynamically stable isotropic single liquid phase containing a ternary system having three components comprising an oily component, an aqueous component and a surfactant, and, in the other case ("microemulsion in the broad sense"), among the thermodynamically unstable typical emulsion systems, the term microemulsion also comprises emulsions that have transparent or translucent appearances on account of their smaller particle sizes (Satoshi Tomomasa, et al., Oil Chemistry, vol. 37, No. 11 (1988), p. 48-53). In the present context, the term "microemulsion" denotes a "microemulsion in the narrow sense", i.e. a thermodynamically stable isotropic single liquid phase.

The microemulsion denotes a state of a microemulsion of O/W (oil-in-water) type in which the oil is dissolved by micelles, a microemulsion of W/O (water-in-oil) type in which the water is dissolved by inverse micelles, or a bicontinuous microemulsion in which the number of associations of surfactant molecules tends to infinity such that the aqueous phase and the oily phase both have a continuous structure.

The microemulsion may have a dispersed phase with a number-average diameter of 100 nm or less, preferably 50 nm or less and more preferably 20 nm or less, measured by laser particle size analysis.

The term "nanoemulsion" presently denotes an emulsion characterized by a dispersed phase with a size of less than 350 nm, the dispersed phase being stabilized by a crown of the non-ionic surfactants (a) and (b) which may optionally form a liquid crystal phase of lamellar type, at the dispersed phase/continuous phase interface. In the absence of specific opacifiers, the transparency of nanoemulsions is due to the small size of the dispersed phase, this small size being able to be obtained by means of using mechanical energy and in particular a high-pressure homogenizer. In one particular embodiment of nanoemulsion according to the invention, said nanoemulsion is stabilized by, in addition to the non-ionic surfactants (a) and (b), the anionic surfactant(s) (f) which in particular allow repulsion between the drops of dispersed phase.

Nanoemulsions may be distinguished from microemulsions by their structure. Specifically, microemulsions are thermodynamically stable dispersions formed, for example, from swollen micelles of non-ionic surfactants (a) and (b) with oil(s). Furthermore, microemulsions do not require substantial mechanical energy to be prepared. The microemulsion may have a dispersed phase with a number-average diameter of 300 nm or less, preferably 200 nm or less and more preferably 100 nm or less, measured by laser particle size analysis.

The cosmetic composition according to the present invention may be in the form of an O/W nanoemulsion or microemulsion, a W/O nanoemulsion or microemulsion, or a bicontinuous emulsion. It is preferable for the cosmetic composition according to the present invention to be in the form of an O/W nanoemulsion or microemulsion.

It is preferable for the cosmetic composition according to the present invention to be in the form of an O/W emulsion.

The mean size of the droplets of the oily phase is measured concentrated by dynamic light scattering (DLS) with a Vasco particle size analyser.

These measurements are taken on the undiluted emulsion.

The number-average size (μm) of the droplets of oily phase of the composition of the invention is less than 300 nm, preferably from 10 nm to 150 nm and more preferably from 20 nm to 100 nm.

Process and Use

A further subject of the invention is a process for the cosmetic treatment of keratin materials, comprising the application to the keratin materials, in particular the skin, of a composition according to the invention as described previously.

Said cosmetic treatment process is non-therapeutic.

In one embodiment, said composition according to the invention does not comprise hesperetin.

More particularly, a subject of the invention is also a cosmetic treatment process for caring for, making up and/or cleansing keratin materials, in particular the skin, comprising the application to said keratin materials, in particular the skin, of a composition according to the invention as described previously.

Said cosmetic treatment process for caring for, making up and/or cleansing the skin is non-therapeutic.

More particularly, a subject of the invention is also a non-therapeutic cosmetic process for reducing the shininess and/or the sheen of keratin materials such as facial and/or bodily skin, comprising at least one step of topical application to the keratin materials, such as the skin, of a composition according to the invention as described previously.

A subject of the invention is also the cosmetic use of a composition according to the invention as defined previously, for caring for, making up and/or cleansing keratin materials.

More particularly, a subject of the invention is also the use of a composition according to the invention as defined above, for reducing the shininess and/or the sheen of facial and/or bodily skin.

According to the invention, the term "keratin materials" is intended to mean the skin, of the body, face and/or area around the eyes, the lips, the nails, the mucous membranes, or any other area of bodily skin. More particularly, the keratin material according to the invention is the skin.

The term "skin" is intended to mean all of the skin of the body, and preferably the skin of the face, neckline, neck, arms and forearms, or even more preferably still the skin of the face, in particular of the forehead, nose, cheeks, chin and area around the eyes.

By way of example, the composition according to the invention may be intended to be administered topically, i.e. by application at the surface of the keratin material under consideration, such as the skin under consideration, optionally by application of a transdermal patch containing it.

The cosmetic composition according to the present invention may be used for a non-therapeutic process, such as a cosmetic process, for treating the skin, the mucous membranes, the nails or the eyelids, by application to the skin, the mucous membranes, the nails or the eyelids.

The present invention also relates to a use of the cosmetic composition according to the present invention, in its native form or in care products and/or washing products and/or makeup products and/or makeup-removing products for bodily and/or facial skin and/or the mucous membranes and/or the nails and/or the eyelids.

The care product may be a lotion, a cream, a hair tonic, a hair conditioner, a sunscreen, and the like. The cleansing product may be a facial cleanser, a hand cleanser, and the like. The makeup product may be a foundation, a mascara, a lipstick, a lip gloss, a face powder, an eyeshadow, a nail varnish, and the like. The makeup-removing product may be a makeup-cleansing product, and the like.

The expressions "between . . . and . . . " and "ranging from . . . to . . . " or "at least . . . " or "at the least of . . . " should be understood as being limits inclusive, unless otherwise specified.

The present invention is described in greater detail by means of examples, which should not, however, be considered as limiting the scope of the present invention.

The compounds are indicated as their chemical name or their INCI name.

The amounts of the ingredients are expressed as weight percentages.

EXAMPLE 1: COSMETIC COMPOSITION ACCORDING TO THE INVENTION

A facial care lotion having the following composition was prepared:

| Ingredients | Composition according to the invention | PHASES |
|---|---|---|
| CAPRYLOYL SALICYLIC ACID | 0.3 | A |
| TRIETHANOLAMINE | 0.24 | |
| C-β-D-xylopyranoside-2-hydroxypropane (MEXORYL SBB ® from Chimex) | 9 | |
| SODIUM HYALURONATE (RENOVHYAL LO ® from Soliance) | 0.52 | |

-continued

| Ingredients | Composition according to the invention | PHASES |
|---|---|---|
| SILICA MICROSPHERES (SUNSPHERE H 51 ® from-AGC SI-TECH) | 4 | |
| PHENOXYETHANOL | 0.5 | |
| ISOSTEARYL NEOPENTANOATE (CERAPHYL 375 ® from-ISP) | 4 | |
| WATER | 31.78 | |
| GLYCEROL | 7 | |
| OCTANE-1,2-DIOL (MINACARE OCTIOL ® from MINASOLVE) | 0.5 | |
| Polyglyceryl-2 laurate or PG-2 laurate (SUNSOFT Q-12D-C ® from Taiyo Kagaku) | 2 | |
| Sodium N-methylstearoyltaurate or SODIUM METHYL STEAROYL TAURATE (Nikkol SMT ® from Nikko) | 0.2 | |
| Polyglyceryl-5 laurate or PG-5 laurate (SUNSOFT A-121E ® from Taiyo Kagaku) | 4 | |
| BIS-PEG-18 METHYL ETHER DIMETHYL SILANE (DOW CORNING 2501 COSMETIC WAX ® by the company Dow Corning) | 1 | |
| BUTYLENE GLYCOL | 17 | |
| Ammonium Acryloyldimethyltaurate/ Steareth-25 Methacrylate Cross-polymer) sold under the name Aristoflex HMS ® by the company Clariant. | 0.6 | B |
| crosslinked copolymer of $C_{10}$-$C_{30}$ alkyl acrylate and of (meth)acrylic acid (TEGO CARBOMER 841 SER from EVONIK GOLDSCHMIDT comprising 100% of active material) | 0.2 | C |
| Crosslinked methacrylic acid/ethyl acrylate copolymer (CARBOPOL AQUA SF-1 POLYMER ® from Lubrizol comprising 30% of copolymer and 70% of water) | 0.95 | D |
| SODIUM HYDROXIDE | 0.02 | |
| ALCOHOL | 5 | E |
| Polysilicone-11 and Cyclohexasiloxane (Gransil RPS-D6 ® from the company Grant Industries comprising 87% of Cyclohexasiloxane and 13% of Polysilicone-11) | 10 | |
| DIMETHICONE and DIMETHICONOL (Xiameter PMX-1503 FLUID ® by the company Dow Corning) | 1 | |
| Fragrance | 0.2 | |

Preparation Method:

Preparation Method

Phase A is heated to 60° C. with stirring.

At 60° C., phase B is added with stirring, followed by phase C at around 40° C. and finally phase D around 30° C.

At ambient temperature, predispersed phase E is added.

The stability was evaluated by observing the various compositions.

It was in particular considered that the composition was:

Stable: at 24 h, when a homogeneous product was observed.

Unstable: at 24 h, when 2 phases were observed, often a clear pellet and a considerable white supernatant.

The composition of Example 1, in accordance with the invention, is single-phase and clear, and remains stable and homogeneous at 24 H and after storage for 3 months at 40° C.

EXAMPLE 2: EVALUATION OF THE COSMETIC PROPERTIES SUCH AS THE SENSORALITY OF A COMPOSITION, SUCH AS THE TACKINESS AND/OR THE SLIP DURING APPLICATION

The sensory aspect, such as the tackiness, during application of the compositions, such as the composition according to Example 1, to the skin was evaluated by a panel of about twenty trained experts (according to a procedure comprising standardized body movement for the application).

The evaluation criteria are standardized and graded on a scale of 1 to 15 (from having no tackiness and/or slip to having high tackiness and/or slip).

An amount of 0.05 ml of composition is deposited on one cheek in 10 rounds of application. The hands are washed with water and soap then dried before evaluating various parameters, including the tackiness and the slip evaluated 2 minutes after application.

The tackiness effect of the composition is evaluated tactilely. This criterion is evaluated by placing the back of the hand against the face and then removing it from the face. The slip is the sensation of non-rubbing to the touch, evaluated by slight movement of the back of the fingers on the area of the face where the product was applied.

| Evaluation of the slip and of the tackiness after application | Composition of Example 1 in accordance with the invention |
|---|---|
| Tackiness - 2 minutes after application | 5** |
| Slip - 2 minutes after application | 7** |

**Significant difference at 5%

It was observed that, surprisingly, the composition of Example 1 according to the invention exhibits, after application to the skin, good sensory properties, in particular it is not very tacky and has a correct slip.

The invention claimed is:

1. A composition in the form of a nanoemulsion or microemulsion, comprising:
    a first fatty acid ester of polyglycerol (a) which is chosen from a fatty acid ester of polyglycerol formed from at least one acid comprising an alkyl or alkenyl chain containing from 12 to 20 carbon atoms and from 3 to 6 glycerol units;
    a second fatty acid ester of (poly)glycerol (b) which is chosen from a fatty acid ester of (poly)glycerol formed from at least one acid comprising an alkyl or alkenyl chain containing from 6 to 18 carbon atoms and from 1 to 3 glycerol units;
    wherein the total amount of fatty acid ester(s) of polyglycerol (a)] and fatty acid ester(s) of (poly)glycerol (b) is 0.5% to 40% by weight relative to the total weight of the composition;
    from 0.1% to 5% by weight relative to the total weight of the composition of at least one organopolysiloxane elastomer;
    from 0.2% to 5% by weight of active material relative to the total weight of the composition of at least two acrylic acid-based polymers that are different from one another;
    from 0.1% to 3% by weight relative to the total weight of the composition of at least one amphiphilic polymer comprising at least one 2-acrylamidomethylpropane-sulfonic acid (AMPS) unit;

from 1% to 50% by weight relative to the total weight of the composition of at least one oil; and 30% to 90% by weight relative to the total weight of the composition of water.

2. The composition according to claim 1, wherein the first fatty acid ester of polyglycerol (a) is chosen from polyglyceryl monolaurate comprising from 4 to 6 glycerol units, polyglyceryl monooleate comprising from 4 to 6 glycerol units, polyglyceryl mono(iso)stearate comprising from 4 to 6 glycerol units, polyglyceryl monolaurate comprising from 4 to 6 glycerol units, polyglyceryl dioleate comprising from 4 to 6 glycerol units, polyglyceryl monomyristate comprising from 4 to 6 glycerol units, and mixtures thereof.

3. The composition according to claim 1, wherein the second fatty acid ester of (poly)glycerol (b) is chosen from (poly)glyceryl monolaurate comprising from 1 to 3 glycerol units, (poly)glyceryl monocaprate comprising from 1 to 3 glycerol units, (poly)glyceryl monocaprylate comprising from 1 to 3 glycerol units, (poly)glyceryl monostearate comprising from 1 to 3 glycerol units, and mixtures thereof.

4. The composition according to claim 1, wherein the first fatty acid ester of polyglycerol (a) has an HLB value of 10 to 13, and/or in that the second fatty acid ester of (poly)glycerol (b) has an HLB value of 8 to 10.

5. The composition according to claim 1, wherein the first fatty acid ester of polyglycerol (a) is a polyglyceryl monolaurate comprising 4 to 6 glycerol units, and the second fatty acid ester of (poly)glycerol (b) is chosen from (poly)glyceryl monolaurate comprising from 1 to 3 glycerol units and (poly)glyceryl monocaprate comprising from 1 to 3 glycerol units.

6. The composition according to claim 1, which also comprises at least one anionic surfactant of formula (II):

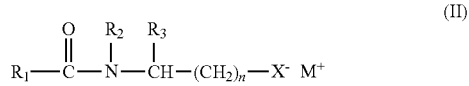

(II)

in which:

R$_1$ is a, saturated or unsaturated, linear or branched alkyl chain containing from 7 to 17 carbon atoms, R$_2$ is H or a methyl, R$_3$ is H, COO$^-$M$^+$, CH$_2$COO$^-$M$^+$or COOH, n is from 0 to 2, X is COO$^-$ or SO$_3^-$ and M independently represents H, sodium, potassium or sorbitan.

7. The composition according to claim 1, wherein the total amount of fatty acid ester(s) of polyglycerol (a) to the total amount of fatty acid ester(s) of (poly)glycerol (b) weight ratio ranges from 0.2 to 10.

8. The composition according to claim 1, which also comprises at least one polyol (c) at a total content of greater than or equal to 15% by weight relative to the total weight of the composition.

9. The composition according to claim 8, wherein said polyol(s) is (are) present in a content ranging from 15% to 60% by weight relative to the total weight of the composition.

10. The composition according to claim 1, wherein said oil(s) is (are) chosen from the group constituted of oils of plant origin, mineral oils, synthetic oils, silicone oils and hydrocarbon-based oils.

11. The composition according to claim 1, which comprises one or more silicone oils chosen from polydimethylsiloxanes containing oxyethylene groups, cyclopolydimethylsiloxanes and polydialkylsiloxanes.

12. The composition according to claim 1, wherein the total amount of fatty acid esters of polyglycerol (a) and (b)/total amount of oil(s) weight ratio ranges from 0.2 to 10.

13. The composition according to claim 1, which comprises at least one organopolysiloxane elastomer which is chosen from a gel of silicone elastomer dispersed in a silicone oil.

14. The composition according to claim 1, wherein the acrylic acid-based polymers are at least two crosslinked copolymers of C1-C30 alkyl acrylate and of (meth)acrylic acid, and a crosslinked copolymer of C10-C30 alkyl acrylate and of (meth)acrylic acid.

15. The composition according to claim 1, wherein said amphiphilic polymer(s) comprising at least one 2-acrylamidomethylpropanesulfonic acid unit is (are) the copolymer of AMPS and of ethoxylated stearyl methacrylate.

16. The composition according to claim 1, which is a cosmetic and/or in the form of an oil-in-water (O/W) emulsion, and the oil(s) is (are) in the form of droplets with a number-average particle size of 300 nm or less.

17. The composition according to claim 1, wherein the total amount of organopolysiloxane elastomer(s)/the total amount of acrylic acid-based polymers and of amphiphilic polymer(s) weight ratio ranges from 0.01 to 20.

18. The composition according to claim 1, which is a cosmetic in the form of an oil-in-water (O/W) emulsion, and the oil(s) is (are) in the form of droplets with a number-average particle size of 300 nm or less; wherein the first fatty acid ester of polyglycerol (a) is a polyglyceryl monolaurate comprising 4 to 6 glycerol units, and the second fatty acid ester of (poly)glycerol (b) is chosen from (poly)glyceryl monolaurate comprising from 1 to 3 glycerol units and (poly)glycerol monocaprate comprising from 1 to 3 glycerol units; the total amount of fatty acid ester(s) of polyglycerol (a) to the total amount of fatty acid ester(s) of (poly)glycerol (b) weight ratio ranges from 0.2 to 10; which comprises one or more silicone oils chosen from polydimethylsiloxanes containing oxyethylene groups, cyclopolydimethylsiloxanes (cyclomethicones) and polydialkylsiloxanes; at least one organopolysiloxane elastomer which is chosen from a gel of silicone elastomer dispersed in a silicone oil; wherein the acrylic acid-based polymers are at least two crosslinked copolymers of C1-C30 alkyl acrylate and of (meth)acrylic acid; wherein said amphiphilic polymer(s) comprising at least one 2-acrylamidomethylpropanesulfonic acid unit is (are) the copolymer of AMPS and of ethoxylated stearyl methacrylate.

19. A cosmetic process for treating keratin materials, comprising the application to the keratin materials of a composition according to claim 1.

* * * * *